(12) United States Patent
Landry (10) Patent No.: US 9,572,371 B2
(45) Date of Patent: Feb. 21, 2017

(54) LASER LIGHT DEVICE

(76) Inventor: Forrest Landry, Rancho Santa Fe, CA (US)

( * ) Notice: Subject to any disclaimer, the term of this patent is extended or adjusted under 35 U.S.C. 154(b) by 871 days.

(21) Appl. No.: 13/215,494

(22) Filed: Aug. 23, 2011

(65) Prior Publication Data
US 2013/0051422 A1 Feb. 28, 2013

(51) Int. Cl.
*A24F 1/30* (2006.01)
*H01S 5/022* (2006.01)
*A61L 9/03* (2006.01)
*A61L 9/14* (2006.01)

(52) U.S. Cl.
CPC . *A24F 1/30* (2013.01); *A61L 9/03* (2013.01); *A61L 9/14* (2013.01); *A61L 2209/12* (2013.01); *H01S 5/02288* (2013.01)

(58) Field of Classification Search
CPC ..... A24F 1/30; A61L 9/03; A61L 9/14; A61L 2209/12; H01S 5/02288
USPC .................................................. 372/50.23
See application file for complete search history.

(56) References Cited

U.S. PATENT DOCUMENTS

| | | | | |
|---|---|---|---|---|
| 4,145,122 A | * | 3/1979 | Rinard et al. | 351/210 |
| 5,521,703 A | * | 5/1996 | Mitchell | 356/301 |
| 2002/0085596 A1 | * | 7/2002 | Irie et al. | 372/36 |
| 2010/0319716 A1 | * | 12/2010 | Tao | 131/173 |

* cited by examiner

*Primary Examiner* — Xinning Niu
(74) *Attorney, Agent, or Firm* — ONE LLP (57) ABSTRACT

The embodiments and methods described are directed to a solid-state laser module having a first end, a second end, and a surface between the first end and the second end. A mounting component is placed in communication with at least a portion of the surface of the laser module for selectively securing the laser module to a chamber wall of a chamber.

13 Claims, 7 Drawing Sheets

FIG. 8

LASER LIGHT DEVICE

TECHNICAL FIELD

The embodiments described herein are generally directed to a device and methods of use of a laser light device for making more visible vaporizing herbs or smokeable materials.

BACKGROUND

Smoking of naturally occurring herbs, tobacco, and other substances is a common occurrence in most countries of the world. Vaporization is also an excellent alternative to smoking. Instead of burning the herbs, tobacco, or other products by placing them in the bowl of a pipe, a vaporizer heats the material. This causes the active compounds contained in the plant material being employed to evaporate into a vapor into a chamber of the vaporizer.

Water pipes and other such devices have also been used to enjoy organic materials such as tobacco. The classic water pipe is a single, vertical, elongated open pipe sealed at the bottom portion and open at the upper portion. Water is placed into the elongated pipe so that when the smoker draws on the pipe, smoke is bubbled through the water and enters the inhalation chamber.

It would be desirable to provide a device that produces shaped light to make the vapor or smoke within the chamber more visible to the user. In addition, a compact design would allow the user to easily mount the device on the vaporizer or water pipe.

SUMMARY

In the embodiments and methods described, a solid-state laser module is employed having a first end, a second end, and a surface between the first end and the second end. A mounting component is placed in communication with at least a portion of the surface of the laser module for selectively securing the laser module to a chamber wall of a chamber.

These together with other objects and advantages that become subsequently apparent reside in the details of the construction and operation of the laser light device herein as more fully hereinafter described and claimed, reference being had to the accompanying drawings forming a part thereof, wherein like numerals refer to like parts throughout.

BRIEF DESCRIPTION OF THE DRAWINGS

The features and inventive aspects of the present disclosure will become more apparent upon reading the following detailed description, claims, and drawings, of which the following is a brief description:

DETAILED DESCRIPTION

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

The terms "solid-state laser" and "laser" and any variation thereof as used throughout the specification is defined hereinafter to include and is not limited to: a laser that uses a gain medium that is a solid including crystals, glasses, semiconductors; a diode laser; and the like.

The term "module" and any variation thereof as used throughout the specification is defined hereinafter to include and is not limited to: an assembly of components and associated electronic wiring, which performs a defined task and can be linked with other components to form a larger system.

The term "mounting component" and any variation thereof as used throughout the specification is defined hereinafter to include the exemplary descriptions within the specification and is not limited to: foam, silicon, rubber, brackets, rings, and the like used to selectively secure a laser module to a chamber.

The term "transparent" and any variation thereof as used throughout the specification is defined hereinafter to include and is not limited to: a material that allows objects to be seen through it; allows at least a portion of light to pass through it; and includes translucent material, where objects beyond are not distinctly seen; including glass, plastic; and the like.

The term "vapor" and any variation thereof as used throughout the specification is defined hereinafter to include and is not limited to: particles of moisture or other substance suspended in air and visible as clouds, smoke, and the like.

The term "smoke" and any variation thereof as used throughout the specification is defined hereinafter to include and is not limited to: the product of combustion, consisting of fine particles in the air; any cloud of fine particles suspended in a gas; and the act of smoking tobacco or other substances.

The term "fan" and any variation thereof as used throughout the specification is defined hereinafter to include and is not limited to: light in a generally triangular shape; light in a shape that spreads out; and light visible in a generally triangular shape in the presence of vapor or smoke.

The term "curtain" and any variation thereof as used throughout the specification is defined hereinafter to include and is not limited to: light in a generally rectangular shape; and light visible in a generally rectangular shape in the presence of vapor or smoke.

Referring to FIGS. 1-6, a first exemplary embodiment vaporizer 10 is provided described in U.S. application Ser. No. 12/705,906 filed Feb. 15, 2010, which is incorporated by reference in its entirety including all drawings. A housing 16 is shown having an exhaust tube 18 disposed within an exhaust opening. A generally circular aperture 20 is disposed on the upper surface 22 providing an opening for the selectively placed transparent chamber 24. A battery 25 is disposed in a generally perpendicular relationship to the exhaust tube 18.

Figure 1:
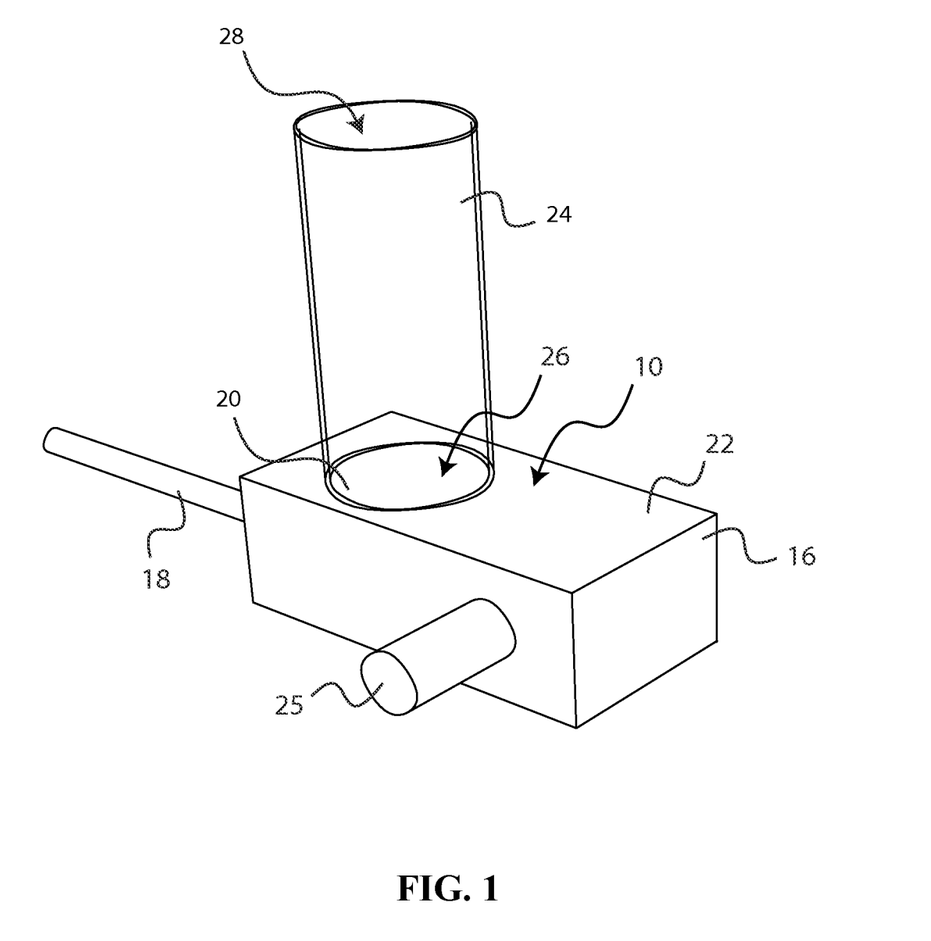
FIG. 1 is a perspective view of a vaporizer device illustrating a transparent chamber placed within the vaporizer's vaporization chamber.

The transparent chamber 24 is added to the exemplary vaporizer 10 to increase the size of the vaporization chamber 26, which receives the vapors formed by the vaporization process. The transparent chamber 24 is also in communication with the exhaust tube 18 during use. The transparent chamber 24 includes a first end 26 disposed within aperture 20 and a second end 28 disposed a desired longitudinal distance from the upper surface 22 of the housing 16. The transparent chamber 24 may be made from plastic, glass, or any transparent or translucent material.

The transparent chamber 24 may also be partially transparent where a portion of the transparent chamber 24 may be transparent or translucent and a portion may block light by being painted or selected from a non-transparent or non-translucent material or color of a material. For example, the upper portion of the transparent chamber 24 may be made from a clear plastic and the lower portion of the transparent chamber 24 may be made from a black plastic.

Figure 2:
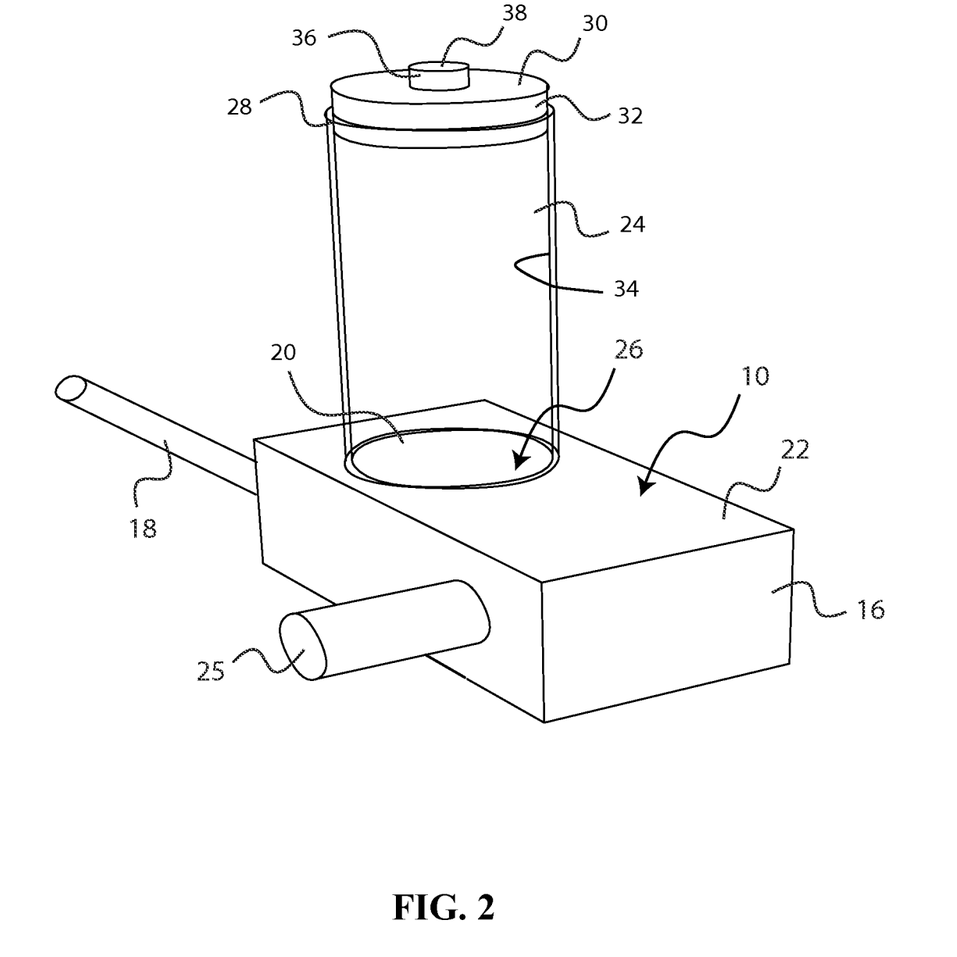
FIG. 2 is a perspective view of the device of FIG. 1 illustrating including an exemplary laser light device disposed within the opening of the transparent chamber.

Referring now to FIG. 2, an exemplary embodiment of a mounting component 30 is shown having an outer surface 32 of the mounting component 30 in mechanical communication with the inner surface 34 of the transparent chamber 24. A user may selectively insert the mounting component 30 into the second end 28 of the transparent chamber 24. The mounting component 30 also includes an aperture disposed generally proximate the center of the mounting component 30 providing an inner surface (not shown) adapted to be in mechanical communication with a module outer surface 36 of a laser module 38. The mounting component 30 secures the laser module 38 proximate the second end 28 of the transparent chamber 24 and provides a closure for the vacuum created in the transparent chamber 24 during use. The mounting component 30 may be made from any type of foam, rubber, plastic, silicon, cork and the like.

Figure 3:
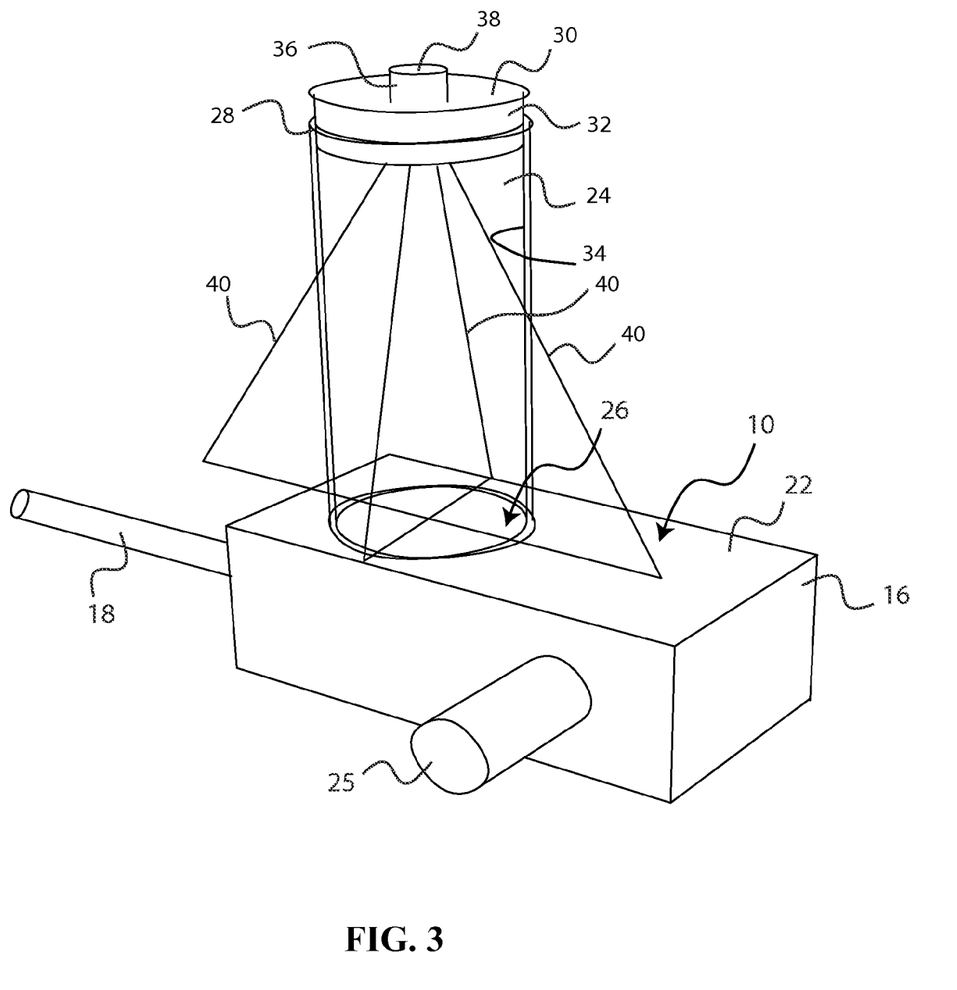
FIG. 3 is a perspective view of the device of FIG. 1 illustrating a fan-shaped light from the laser light device.
Figure 4:
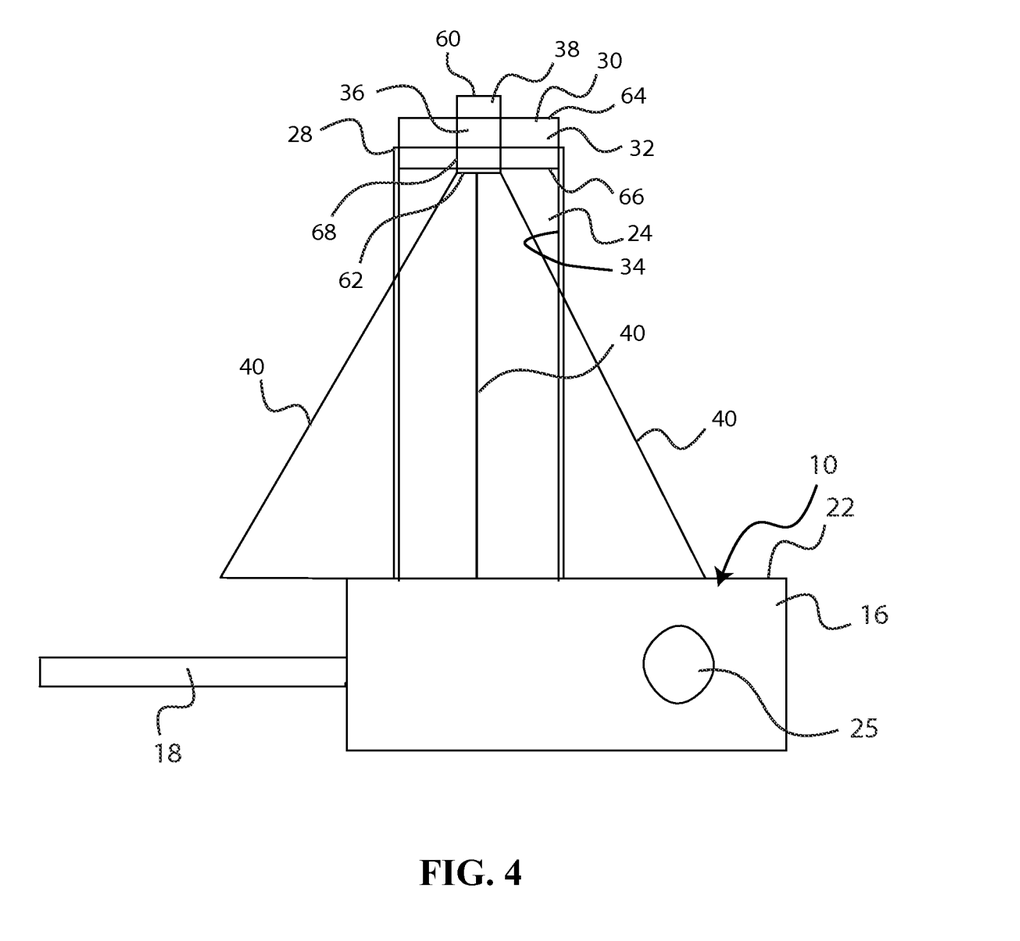
FIG. 4 is a side view of FIG. 3.
Figure 5:
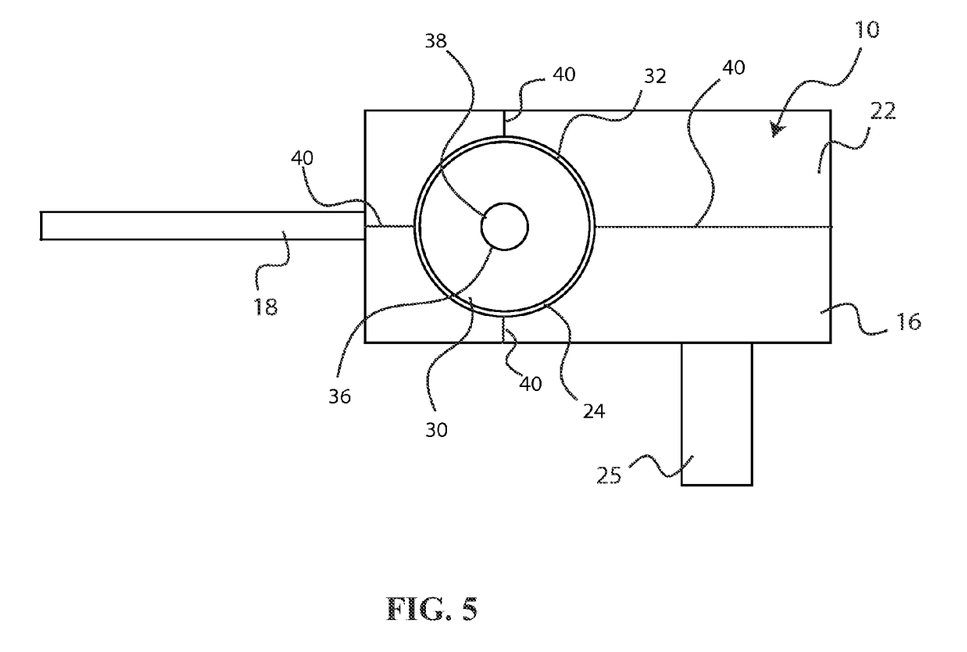
FIG. 5. is a top view of FIG. 3.

Referring to FIGS. 3-5, an exemplary embodiment is provided having a laser module 38 providing a generally fan-shaped light 40 emitting from the laser module 38. The fan-shaped light 40 is emitted proximate the second end 28 of the chamber 24 and extends downwardly toward the upper surface 22 of the housing 16. Portions of the fan-shaped light 40 are shown to extend outside of walls of the transparent chamber 24. The exemplary laser module 38 is shown to produce one fan-shaped light, however, a plurality of fan-shaped lights may be provided. During use, the light from the laser module 38 bisects or crosses the vapor or smoke particles and provides a pleasing image for the user. In addition to a fan-shaped image, other light shaped embodiments include a column, an hour glass, or a curtain of light.

Figure 6:
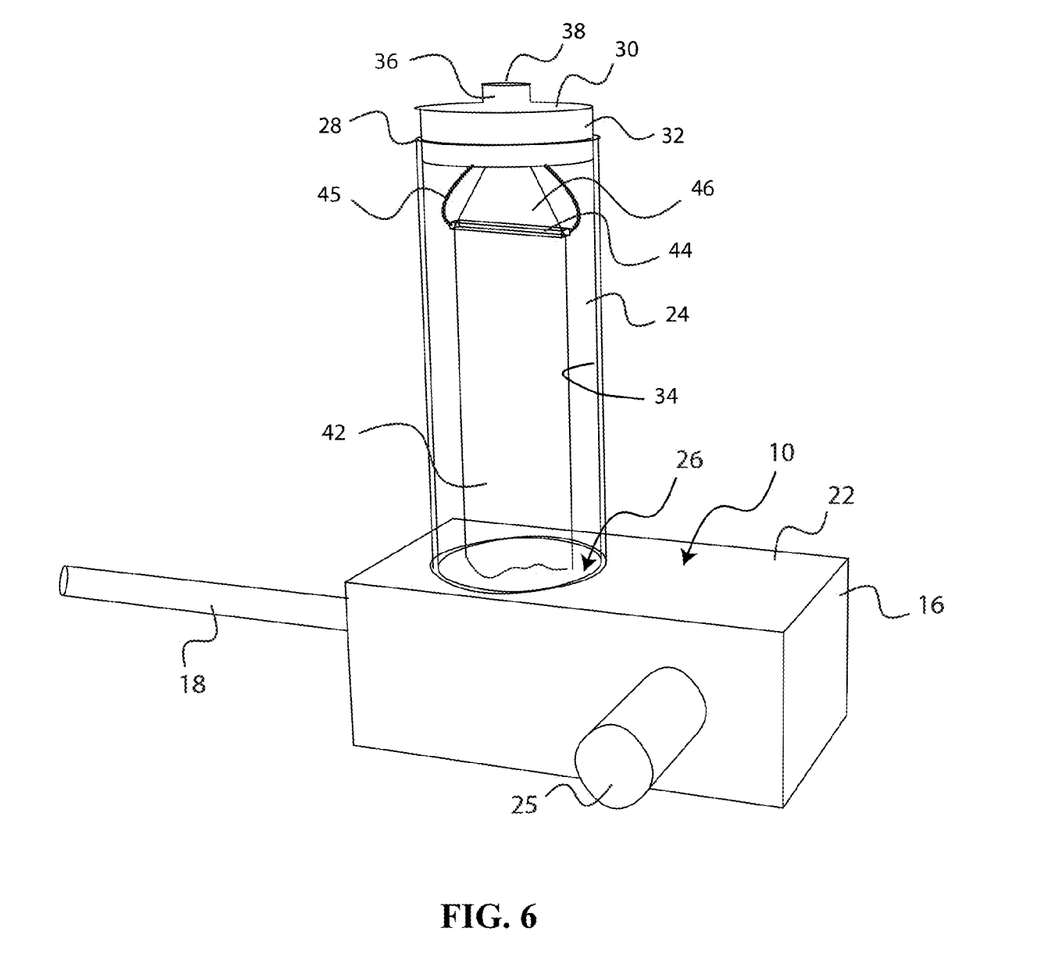
FIG. 6 is a perspective view of a vaporizer device including another exemplary laser light device disposed within the opening of the transparent chamber and showing a curtain-fan light from the laser light device.

Referring to FIG. 6, another exemplary embodiment is shown producing a curtain-shaped laser image 42 along the longitudinal length of the chamber 24. The curtain-shaped laser image 42 is disposed within the transparent chamber 24 unlike the fan-shaped light 40 of FIG. 3 above. The shape of the light may be changed depending on the desired lens 44 used. Here, a plastic, glass, Fresnel, or the like lens 44 is used to convert a fan-shaped light 46 emitting form the laser module 38 to the curtain-shaped light 42 shown by suspending the lens 44 a desired distance from the laser module 38. The lens 44 may be suspended by any mechanism or structure 45 including being disposed within the mounting component 30 (not shown).

The laser module 38 may be selected from any of a variety of off-the-shelf solid-state laser units available including a diode-laser module. One exemplary laser module 38 includes an internal lens that converts a beam of light into the fan-shaped light 40 described above. The laser module 38 may be obtained having batteries built into the laser module 38 or wires for placing the laser module 38 into electrical communication with a power source including but not limited to a battery power source. In addition, an ON/OFF switch may be placed between the laser module 38 and the battery power source for switching the laser module 38 between an ON and OFF position. The ON/OFF switch may also be integrated into the laser module 38.

Figure 7:
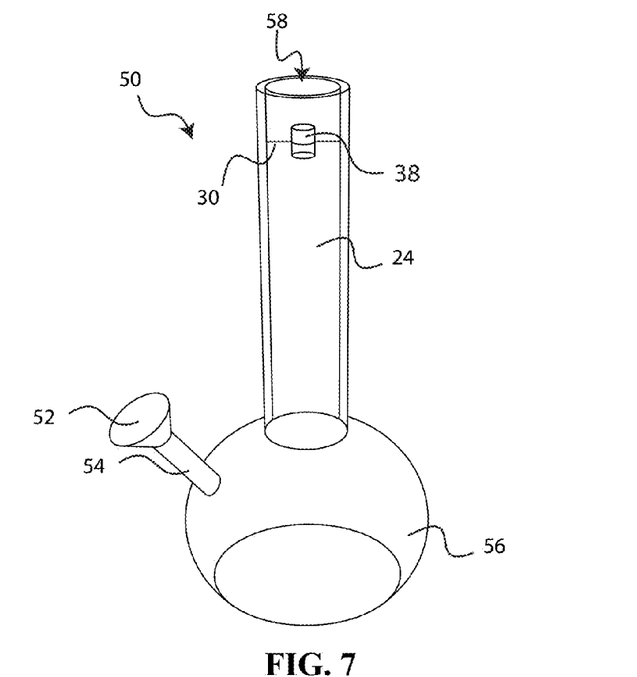
FIG. 7 is a perspective view of a water pipe device illustrating the laser light device disposed within the transparent chamber.
Figure 8:
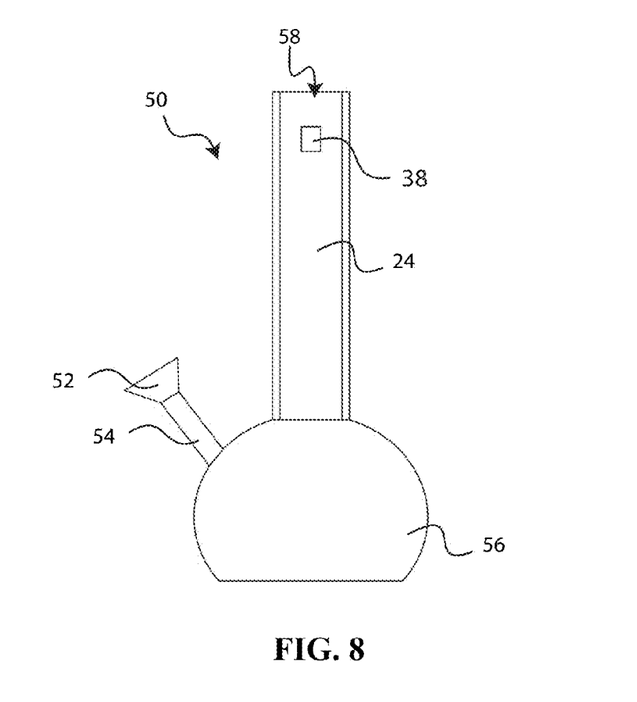
FIG. 8 is a side view of FIG. 7.

Referring not to FIGS. 7 and 8, an exemplary water pipe 50 is shown having the laser module 38 disposed within the walls of the transparent chamber 24. In operation, the smokable material is placed in a bowl 52 where it is heated or burned to obtain the smoke that is drawn through the stem 54 into the water disposed in the water holding area 56. The user of the water pipe 50 draws smoke through the device by application of negative pressure to the opening 58 that draws the smoke through the water in the water holding area 56. The mounting component 30 permits the smoke to pass through the opening 58 while securing the laser module 38 in place.

The mounting component 30 may be made from any material for securing the laser module 38 a desired distance from the opening 58 of the water pipe 50. In one exemplary embodiment, the mounting component 30 is formed from at least one metal wire having at least a first wire end secured to the opening 58 and at least a second wire end secured to the laser module 38. The first wire end may be secured to the opening 58 and the second wire end may be secured to the laser module 38 by any method. In another exemplary embodiment, the mounting component 30 is formed from a material such as metal, wood, cork, and the like having apertures disposed circumferentially around the laser module 38. The mounting component 30 is adapted to secure the laser module 38 within the opening 58 while allowing vapor or smoke to pass through the mounting component 30.

Again, referring to FIGS. 1-8, the solid-state laser module 38 is illustrated having a first end 60, a second end 62, and the surface 36 between the first end 60 and the second end 62. The mounting component 30 is in communication with at least a portion of the surface 36 of the laser module 38 for selectively securing the laser module 38 within the inner surface chamber wall 34 of the chamber 24. The solid-state laser module 38 provides at least one light shape at least partially inside the chamber 24. An exemplary embodiment includes having the light shape be a fan-shape or a column-shape. The device further may include the lens 44 disposed proximate the solid-state laser module 38 for reshaping the light shape from the solid-state laser module 38. In one embodiment, the lens 44 reshapes the light shape from a fan-shape to a curtain-shape.

The mounting component 30 is made from any material including foam, rubber, plastic, silicon, cork, and the like. In an exemplary embodiment, the laser module 38 may include wiring elements for electrical communication with a battery power source. In an exemplary embodiment, the solid-state laser module 38 is a diode laser. In another exemplary embodiment the laser module 38 includes an ON/OFF switch disposed between the solid-state laser module 38 and the battery power source. The chamber 24 may be at least partially transparent or translucent.

A laser display method includes selecting a generally circular mounting component 30 having an upper surface 64, a lower surface 66, and an aperture 68 disposed between the upper surface 64 and the lower surface 68. The method also includes placing the solid-state laser module 38 having the first end 60, the second end 62, and the surface 36 between the first end 60 and the second end 62 into the aperture 68 of the mounting component 30 for securing the solid-state laser module 38 to the inner surface chamber wall 34 of the transparent chamber 24. In one exemplary embodiment, the lens 44 is placed proximate the second end 62 of the solid-state laser module 38 for providing at least one light shape into the transparent chamber 24.

The laser display method may also include selecting the solid-state laser module 38 for providing a fan-shape light or a column-shape light at least partially inside the transparent chamber 24. The lens 44 is placed proximate the solid-state laser module 38 for changing the light shape emitted from the solid-state laser module 38. In one embodiment, the lens 44 changes the light shape from a fan-shape to a curtain-shape. The mounting component 30 may be made from foam, rubber, plastic, silicon, cork and the like.

The laser display method may also include placing the wiring elements for electrical communication with the battery power source proximate the first end 60. In addition, the method may include placing the ON/OFF switch between the solid-state laser module 38 and the battery power source. In one exemplary embodiment, the method includes having the chamber 24 be at least partially transparent or translucent.

The preceding description has been presented only to illustrate and describe exemplary embodiments of the methods and device of the provided disclosure. It is not intended to be exhaustive or to limit the disclosure to any precise form. It will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope. Therefore, it is intended that the disclosure not be limited to the particular embodiment discussed as the best mode contemplated for carrying out the teaching of the disclosure, but that the teaching will include all embodiments falling within the scope of the claims. The disclosure may be practiced otherwise than is specifically explained and illustrated without departing from its spirit or scope. The scope of the disclosure is limited solely by the following claims.

What is claimed is:

1. A laser device for illuminating smoke or vapor within an inhalation chamber of a pipe, water pipe or vaporizer, the chamber being defined by an at least partially transparent tube, with at least some transparent portions of the at least partially transparent tube being substantially free of any opaque reflective coating, the laser device comprising:
    a solid-state laser module having a first end, a second end, and a surface between said first end and said second end; and
    a mounting component in communication with at least a portion of said surface of said laser module for mounting said laser module onto the pipe, water pipe or vaporizer and to position the laser module so as to shine light into the inhalation chamber.

2. The laser device of claim 1 wherein said solid-state laser module provides at least one light shape that is fully formed within the illumination chamber, the light shape being selected from the group consisting of a fan-shape and a column-shape.

3. The laser device of claim 1, further comprising a lens disposed proximate said solid-state laser module for reshaping a light shape from said solid-state laser module.

4. The laser device of claim 3, wherein said lens reshapes the laser's light to a light shape that is fully formed within the inhalation chamber, the light shape being selected from the group consisting of a fan shape, a curtain shape, a column, and an hour glass.

5. The laser device of claim 1, wherein said mounting component is made from a material selected from the group consisting of foam, rubber, plastic, silicon and cork.

6. The laser device of claim 1, further comprising wiring elements for electrical communication between a battery power source and the laser module.

7. The laser device of claim 1, wherein said solid-state laser is a diode laser.

8. The laser device of claim 6, further comprising an ON/OFF switch disposed between the laser module and the battery power source.

9. The laser device of claim 3, wherein the lens shapes the light into at least two light shapes in different planes.

10. A laser device for illuminating smoke or vapor within an at least partially transparent inhalation chamber of a pipe, water pipe or vaporizer, with at least some transparent portions of the chamber being substantially free of any opaque reflective coating, the laser device comprising:
    A solid-state laser module having a first end, a second end, and a surface between said first end and said second end;
    A lens proximate said second end for providing at least one light shape;
    A mounting component in communication with at least a portion of said surface for securing said solid-state laser module within a chamber wall of a transparent chamber where said transparent chamber is adapted to receive smoke or vapor; and
    A battery power supply in electrical communication with said laser module proximate said first end.

11. The laser device of claim 1 wherein the tube that defines the inhalation chamber has a first end and a second end and is a part of the laser device, and the first end of the tube is adapted to engage the vaporization chamber of a vaporizer.

12. The laser device of claim 1 wherein the inhalation chamber section is formed as an integral part of the pipe, water pipe or vaporizer.

13. The laser device of claim 1 wherein the tube has a circular cross section.

* * * * *